United States Patent [19]

Hoke

[11] Patent Number: 5,135,847
[45] Date of Patent: Aug. 4, 1992

[54] SUBSTRATE COMPOSITION FOR ALKALINE PHOSPHATASE AND METHOD FOR ASSAY USING SAME

[75] Inventor: Randal A. Hoke, Cary, N.C.

[73] Assignee: Becton, Dickinson and Company, Franklin Lakes, N.J.

[21] Appl. No.: 272,844

[22] Filed: Nov. 18, 1988

[51] Int. Cl.[5] .................... C12G 1/00; C12N 11/00; A61K 39/12
[52] U.S. Cl. .......................................... 435/5; 435/4; 435/810; 435/174; 435/176; 435/177; 435/317.1; 435/975; 435/7.9; 435/7.94; 435/7.93; 435/7.92; 435/7.72; 435/21; 424/7.1; 424/88; 514/368
[58] Field of Search ............... 435/7, 4, 810, 174, 435/176, 177, 317; 424/8, 12, 88

[56] References Cited

U.S. PATENT DOCUMENTS

| | | | |
|---|---|---|---|
| 4,322,495 | 3/1982 | Kato | 435/7 |
| 4,693,970 | 9/1987 | O'Connell | 435/7 |
| 4,847,194 | 7/1989 | Quante | 435/7 |

FOREIGN PATENT DOCUMENTS 0228663 12/1986 European Pat. Off.

OTHER PUBLICATIONS

Ponder, B. A. et al., The J. Histoch. Cytochem. vol. 29, No. 8, pp. 981–984 (1981).
Voller, *The Enzyme Linked Immunosorbent Assay (ELISA)*, MPEP Section 608.01(v).
USAN and the USP Dictionary of Drug Names.

*Primary Examiner*—Robert A. Wax
*Assistant Examiner*—Bradley L. Sisson
*Attorney, Agent, or Firm*—Richard E. Brown

[57] ABSTRACT

A composition contains levamisole and a substrate for alkaline phosphatase in a high pH buffer including 2-amino-2-methyl-1-propanol. The composition may be included in a kit of materials useful in performing an immunoassay in which intestinal alkaline phosphatase is the label. The invention includes a method for detection of a viral antigen by an immunoassay including intestinal alkaline phosphatase as the label and the composition of the invention to provide stabilized levamisole to inhibit nonintestinal alkaline phosphatase.

7 Claims, 1 Drawing Sheet

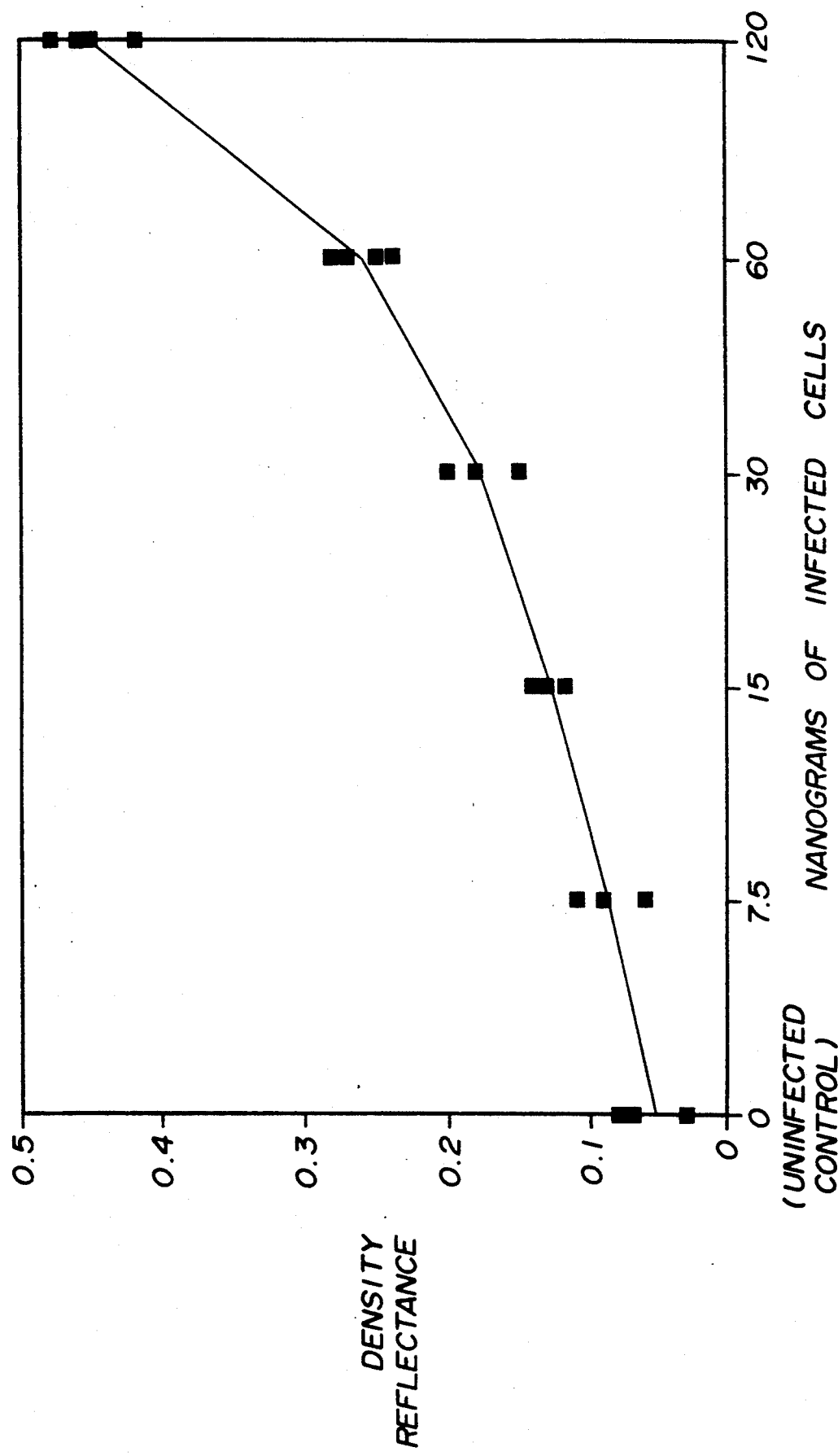

SUBSTRATE COMPOSITION FOR ALKALINE PHOSPHATASE AND METHOD FOR ASSAY USING SAME

BACKGROUND OF THE INVENTION

1. Field of the Invention

This invention relates to an immunoassay of an analyte and materials used therein, and more particularly relates to a method and materials for an immunoassay using a novel alkaline phosphatase substrate composition.

2. Background of the Invention

Assay systems which are both rapid and sensitive have been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer. Immunoassay procedures may be carried out in solution or on a solid support and may be either heterogeneous, requiring a separation of bound tracer from free (unbound) tracer or homogeneous in which a separation step is not required.

Enzymes have often been used as labels in immunoassay. In conventional enzyme immunoassay (EIA), an enzyme is covalently conjugated with one component of a specifically binding antigen-antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

Enzymes to be used in an immunoassay must be stable, highly reactive, available in a highly puried form, yield stable conjugates (tracers) and be inexpensive, safe and convenient to use. An enzyme which meets these criteria and is often used in immunoassay is alkaline phosphatase (AP).

AP occurs in substantially all animal species, and, in mammals, occurs in two forms. One form is widely distributed in a variety of tissues while the other is confined to the intestine.

AP catalyzes the cleavage of phosphate groups from generally colorless phosphorylated substrates to give colored products. Since the enzyme is active at alkaline pH, assay systems using AP generally include a buffer which maintains the pH of the assay medium in the range 7-9.

Levamisole, (−)2,3,5,6-tetrahydro-6-phenylimidazo[1,2-b]thiazole, is well known to be a potent inhibitor of AP from several mammalian tissue types. It is, however, approximately 100-fold less potent toward AP from the intestine (Van Belle, *Biochim. et Biophys. Acta.*, 289, 158 (1972).

Advantage has been taken of this selectivity in immunoassay. When used in an assay, levamisole does not interfere with the specific immuno signal generated by calf intestinal A but does reduce the nonspecific signal which arises from any nonintestinal AP which may be present in a clinical sample. Morris et al., in the *Journal of Immunological Methods*, 68, 11 (1984) discloses detection of the binding of monoclonal antibodies to antigens on the surface of whole cells with a conjugate of calf intestinal AP and goat anti-mouse Igb in the presence of a substrate and levamisole added to inhibit AP of nonintestinal origin.

Ponder et al. in the *Journal of Histochemistry and Cytochemistry*, 29, 981 (1981), discloses detection of mouse H2 antigen in tissue slices by incubating the tissue slices with anti mouse H2 antibody and treating with an intestinal AP labeled conjugate followed by a substrate for the enzyme and levamisole to inhibit nonintestinal AP. In the Ponder et al. method, levamisole at a concentration of 1 mM is added to a filtered AP substrate solution prior to combining the substrate with the tissue slices.

Levamisole, while useful in EIA as disclosed in the above patents, is known to be unstable at alkaline pH. Dickinson et al., in *Analyst*, 96, 248 (1971), have shown that levamisole is rapidly decomposed at elevated temperature, and that at pH 7.9, it is decomposed 70 times faster than at pH 2. Accordingly, up until the present invention, levamisole and the high pH assay buffer required for AP activity could not be premixed prior to performing the assay. Significant advantages in time, cost and assay convenience which accrue from premixing assay reagents thus could not be achieved. The present invention is directed to overcoming this deficiency in prior art assays.

SUMMARY OF THE INVENTION

A composition useful in performing an immunoassay for an analyte using AP as the label includes a member of the 6-phenyltetrahydroimidazo-[1,2-b]thiazole class stabilized in a high pH buffer containing a particular amine. The preferred thiazole is levamisole and the preferred buffer includes 2-amino-2-methyl-1-propanol (AMP) and a substrate for AP.

Another aspect of the invention is an immunoassay for an analyte using the composition of the invention and intestinal AP as the label wherein the levamisole in the composition inhibits non-intestinal AP. In the preferred assay of the invention, a viral antigen is captured onto a solid support and contacted with a specific antibody conjugated to intestinal AP. In the present disclosure, the term inert protein means any protein which may be affixed to the solid support but which does not react substantially with any other component of the assay.

The invention includes a kit of materials including the composition useful in performing an assay of the invention.

Inclusion of levamisole in an assay using intestinal AP as the label significantly enhances the assay sensitivity by inhibiting nonintestinal AP which may be present in a body sample and which otherwise would cause nonspecific dephosphorylation of the AP substrate. Since levamisole is unstable at the alkaline pH required for AP activity, in prior art disclosures it is added immediately prior to assay substrate. By providing a composition containing levamisole stabilized at the desired pH of the assay with the particular buffer, the invention makes it possible to mix the levamisole substrate and buffer with sufficient shelf life stability at the time of manufacture and thereby provide the analyst with assay accuracy and convenience consequent to handling only one reagent solution.

BRIEF DESCRIPTION OF THE DRAWING

The Figure illustrates the results of an assay for Respiratory Syncytial Virus (RSV) in accordance with the method of the invention.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The invention provides a new composition useful in assays which includes intestinal AP as the label and levamisole as an inhibitor of any nonintestinal AP which may be present in the sample to be assayed. The invention will be described in terms of levamisole, which is the preferred inhibitor of nonintestinal AP; however, it is understood that any other compound of the imidazo[1,2-b]thiazole class which selectively inhibits nonintestinal AP is contemplated to fall within the scope of the invention.

Levamisole is the generic name of an anthelmintic which has been in veterinary use for many years. Chemically it is (−)2,3,5,6-tetrahydro-6-phenylimidazo[1,2-b]thiazole, and many analogues are known. For example, analogues with substituents such as lower alkyl of 1 to 6 carbon atoms and halogen groups such as chloro and bromo on the pendent phenyl ring are inhibitors of nonintestinal AP and are included within the scope of the present invention. It is also understood that, while the invention will be described in terms of levamisole, the racemic form of levamisole, known generically as tetramisole, may also be used in the invention.

In accordance with the invention, it has been found that levamisole, which hydrolyzes when in solution of pH 4 or greater, may be stabilized at the alkaline pH required by AP by combining it in a composition which includes selected high pH amine buffers. The composition includes the buffer, levamisole, the substrate for AP, and optionally contains magnesium chloride. The concentration of levamisole in the composition may be about 0.1 to 100 mM preferably about 4 to 30 mM.

The buffer of the invention may be any high pH amine buffer in which levamisole is substantially stable. Suitable buffers are triethanolamine, 2-amino-2-methyl-1,3-propanediol (AMPD) and, preferably, AMP. The amine may be present in the buffer at a concentration of about 1–100, preferably about 40–60 millimolar.

Suitable substrates for AP which may be included in the composition are phosphate esters of a nitrophenol, preferably p-nitrophenol. Preferred substrates are phosphate esters of 3-hydroxyindoles which, upon dephosphorylation, undergo oxidative coupling to colored indoxyls. Exemplary of such substrates are 5-bromo-4-chloro-3-indolyl phosphate, and preferably, 3-indolyl phosphate. The substrate may be present in the composition in a concentration of about 0.1 to 100 millimolar, preferably about 1 to 50 millimolar. The most preferred buffer is 50 mM AMP, pH 9.8.

Preferred compositions additionally contain magnesium chloride in a concentration of about 0.1 to 2.0 millimolar, preferably about 0.5 to 1.0 millimolar.

The composition of the invention is particularly suited to immunoassays using intestinal AP as the label component of the tracer. Immunoassay procedures in which AP catalyzes the dephosphorylation of a substrate are well known in the art, and any immunoassay procedure which includes inhibition of nonintestinal AP by the levamisole component of the composition is contemplated to fall within the scope of the invention.

In general, the immunoassay of the invention may be used to determine an antigen, an antibody or a hapten. In this disclosure, the substance to be determined is referred to as the analyte. The only limitation on the analyte is that it should be possible to obtain an antianalyte which binds substantially specifically to the analyte. Thus, if the analyte is an antigen, a suitable antianalyte would be a specific antibody. If the analyte is a hapten, a suitable antianalyte would be an antihapten antibody. If the analyte is an antibody, a suitable antianalyte would be a specific anti antibody. Antibodies useful in the invention as antianalytes may be either monoclonal or polyclonal. Raising of specifically binding antibodies is well known in the art and no further description is needed for a full understanding of this aspect of the invention.

Analytes which may advantageously be assayed using the composition of the invention may be from any source, and may be an antigen, an antibody or a hapten. For example, the analyte may be an antigen present in a body fluid, or it may be isolated from a body fluid and subsequently introduced into a different liquid, such as a buffer. In other cases, the analyte may be from a source other than a body fluid, as, for example, a culture of microorqanisms or a cellular extract thereof. Preferred analytes are antigens, most preferably viral antigens present in a body fluid, such as Herpes simplex virus (HSV), Adenovirus, Influenza A virus, Parainfluenza 3 virus and RSV.

The immunoassay of the invention may be carried out by any conventional sandwich or competitive procedure as known in the art. The assay may be either heterogeneous or homogeneous, and may be carried out in the liquid phase or on a solid support. For example, in a typical sandwich assay, a capture antibody may be affixed to a solid support such as a dipstick, membrane, microtiter plate well or the inside wall of a tube. Preferably, the antibodycoated support is further coated with an inert protein, such as casein or albumin to block substantially all remaining binding sites on the support and thereby suppress nonspecific binding of tracer directly to the support. Blocking with an inert protein is conventional in the immunoassay art.

A solution suspected of containing an antigen is added to the antibody coated and blocked support and conditions conducive to binding the antigen to the antibody are provided. (In this disclosure, antigen bound to antibody is hereinafter called the bound fraction.) A tracer including a second antibody labeled by covalent conjugation to intestinal AP is added. After binding of the second antibody to the antigen, the solid support having affixed thereto an antibody-antigen labeled antibody bound fraction is contacted with the composition of the invention. The substrate in the composition is dephosphorylated by the AP component of the bound tracer on the solid support to form a color. The color is indicative of the presence of the antigen and the intensity of the color is directly proportional to the concentration of the antigen in the liquid.

In a typical competitive assay of the invention, a limited quantity of the antibody on the solid support may be contacted with the liquid suspected of containing the antigen and a tracer which includes a known quantity of the antigen having intestinal AP conjugated thereto. The antigen and enzyme-labeled antigen bind to the antibody on the support in direct proportion to their concentrations in the solution. Thus, after binding, the support contains an antibody antigen bound fraction and an antibody-AP-labeled antigen bound fraction. After separation of the support from the assay fluid phase, the bound fractions on the support may be contacted with the AP substrate to cause formation of a color. However, in the competitive assay of the invention, the color formed is inversely proportional to the concentration of antigen in the liquid.

In the preferred assay of the invention, the sample suspected of containing viral antigen is incubated directly with the solid support, i.e., no capture antibody is used. It has been found that viral antigens may be absorbed directly onto the solid support and subsequently assayed using intestinal AP as the label and levamisole to inhibit nonintestinal AP. In this embodiment of the invention, the solid support having antigen absorbed thereon may be blocked with an inert protein, as described above, or the support may be preblocked with the inert protein and the antigen absorbed directly onto the preblocked support surface.

The composition of the invention may be included as part of a kit of materials useful for performing an immunoassay for an analyte. The kit may include a solid support optionally having a capture antianalyte immobilized thereon, a tracer for the analyte including intestinal AP and the composition of the invention. The composition included in the kit may contain levamisole, a buffer of the invention, a substrate for AP and optionally may contain magnesium chloride. The kit may additionally include containers for the assay reagents and implements, such as vials, droppers and the like useful in performing an assay using the composition of the invention.

The following Examples are provided to further describe the invention but are not to be construed as limitative of the invention.

EXAMPLE I

Stability of Levamisole in Various Buffers

Various buffers were prepared at 100 mM concentrations, containing 1 mM magnesium chloride, and adjusted to pH 9.8. The buffers were autoclaved, spiked with 1 mM levamisole, and placed at 45° C. (accelerated decomposition study). The amount of functional levamisole was subsequently measured by comparing the activity of bovine liver alkaline phosphatase in the presence and absence of 0.05 mM levamisole: A 1 to 20 dilution of the buffered sample was prepared in 1 M diethanolamine, pH 9.8 containing 5 mM p-nitrophenyl phosphate. Bovine liver AP was added and the reaction kinetics were followed at 405 nm. The inhibition constant (Ki) for levamisole acting on the phosphatase was determined at "t =0" using the relation:

$$Ki = \frac{\text{Initial Levamisole} \times \% \text{ Activity}}{100 - \% \text{ Activity}}$$

Subsequently, the amount of functional levamisole was calculated using a rearrangement of the above equation:

$$\text{Levamisole Concentration} = \frac{Ki \times (100 - \% \text{ Activity})}{\% \text{ Activity}}$$

Table I gives the percent of levamisole remaining at various times during the study.

TABLE I

| Buffer | Percent of Functional Levamisole Remaining | | | |
|---|---|---|---|---|
| | Day 0 | Day 3 | Day 9 | Day 17 |
| AMP | 100 | 117.92 | 106.99 | 87.07 |
| AMPD | 100 | 109.86 | 90.20 | 71.74 |
| Triethanolamine | 100 | 94.36 | 66.56 | 37.62 |
| Carbonate | 100 | 63.83 | 32.06 | 13.65 |
| Diethanolamine | 100 | 79.78 | 9.12 | 0.31 |
| Glycine | 100 | 0.08 | 0.02 | 0.00 |

It is seen that the stability of levamisole is substantially greater in AMPD and particularly in AMP than in other buffers.

EXAMPLE II

An accelerated stability of the p-bromo analogue of levamisole was carried out as described in Example I. Since this compound is approximately 10-fold more potent than levamisole, appropriate dilutions were performed to give various buffered stocks containing of 0.1 mM p-bromolevamisole. Table II gives the results of the experiment.

TABLE II

| Buffer | Percent of Functional Levamisole Remaining | | | |
|---|---|---|---|---|
| | Day 0 | Day 3 | Day 9 | Day 17 |
| AMPD | 100 | 73.95 | 37.26 | 18.46 |
| AMP | 100 | 55.43 | 23.87 | 9.60 |
| Triethanolamine | 100 | 58.95 | 22.09 | 7.86 |
| Carbonate | 100 | 44.39 | 10.83 | 2.62 |
| Diethanolamine | 100 | 33.57 | 1.30 | 0.53 |
| Glycine | 100 | 0.29 | 0.25 | 0.00 |

The decomposition of the p-bromo analogue of levamisole is seen to be quite a bit faster than the parent compound, but the order of preferred buffers remains largely unchanged.

EXAMPLE III

Assay for Respiratory Syncyctial Virus (RSV)

A membrane filter stack was assembled with the following configuration:

Top layer—Three micron Immunodyne Immunoaffinity Membrane, (Pall, East Hills, N.Y., #BIA0030HC5). Precoated by immersion in phosphate buffered saline containing 0.3% casein for 30 minutes at ambient temperature.

Next layer—Non-woven rayon sheet (Schleicher and Schuell, Keene, N.H.; #5-S).

Bottom layer—Cellulose absorbent pads (2) (Filtration Sciences, Mount Holly Springs, Penn.; #ED 320-200).

The membrane layers were encased in a plastic holder which includes a receiving well formed above the top layer. Within this well was fitted a flow restriction insert which has an aperture more narrow than the receiving well and sits flush against the top membrane.

An antigen stock was prepared with respiratory syncytial virus (RSV) (Long strain) infected HEp-2 cells diluted in a buffer containing: 250 mM tris(hydroxymethyl)aminomethane hydrochloride (Tris HCl), 150 mM sodium chloride (NaCl), 10 mM ethylene-diaminetetraacetate (EDTA), 4% (v/v) polyoxyethylene sorbitan monolaurate (Tween 20), 1% n-acetyl cysteine, 0.2% sodium azide (NaN$_3$), pH 8.5. Control antigen was prepared in a similar manner from uninfected HEp-2 cells.

A 150 μL aliquot of this antigen (or control) was applied to the device and allowed to drain through the flow restriction insert and onto the top membrane layer. (Liquid is drawn through the top membrane by the capillary action of the supporting absorbent layers.) The flow restriction insert was then removed, and to the device was added 150 μL of a wash solution consisting of 50 mM Tris HCl, 150 mM NaCl, 0.2% NaN$_3$, pH 7.2 (Tris buffered saline (TBS)), additionally containing 1 mg/mL of rabbit IgG.

A solution containing 27 μg/mL of anti-RSV antibody conjugated to alkaline phosphatase was prepared in a buffer containing 50 mM Tris HCl, 100 mM NaCl, 200 mM sodium phosphate, 1% casein, 1 mM magnesium chloride, 0.1 mM zinc chloride, and 1 mM 2-mercaptoethanol, pH 7.5. A 150 μL aliquot of this mixture was added to the device and allowed to absorb into the membrane stack. Following a brief (two minute) incubation, the device was washed with 300 μL of TBS (without IgG).

A 150 μL solution containing 0.33 mg/mL nitroblue tetrazolium, 1% methanol, and 0.2% NaN$_3$ was added to the device. This was followed by the addition of 150 μL of a solution containing 12 mM levamisole in 50 mM 2-amino-2-methyl-1-propanol acetate (AMP HOAc), 0.2% NaN$_3$, mM magnesium chloride, at pH 9.8. Following a five minute incubation at ambient temperature, the color forming reaction was stopped by the addition of 150 μL of a solution containing 200 mM potassium phosphate, 10 mM EDTA, 0.2% NaN$_3$, pH 7.2.

The color density of the resulting membrane was measured with a reflectance densitometer (Gretag, Seattle, Wash., model 183). The results of an experiment performed with a series of antigen dilutions are presented in the Figure.

Thus, the invention provides a buffered composition in which levamisole is stable at the alkaline pH required for AP activity so that advantage may be taken of the ability of levamisole to selectively inhibit nonintestinal AP. Intestinal AP may then be used in an immunoassay of enhanced sensitivity with the advantage of prepackaging the levamisole and AP substrate.

What is claimed is:

1. A kit of materials for performing an assay for an analyte comprising an antianalyte immobilized on a solid support, a tracer including intestinal alkaline phosphatase, said antianalyte binding specifically to said analyte, said tracer binding to one of said analyte and antianalyte, and a buffer containing a substrate for said alkaline phosphatase, a 2,3,4,5-tetrahydro-6-phenylimidazo thiazole, and an amine selected from the group consisting of triethanolamine, 2-methyl-2-amino-1,3-propanedial and 2-amino-2-methyl-1-propanol.

2. The kit of claim 1 wherein said tracer further comprises a reagent selected from the group consisting of analyte and a second antianalyte having said intestinal alkaline phosphatase conjugated thereto.

3. The kit of claim 1 wherein the concentration of said substrate is about 0.1 to 100 millimolar.

4. The kit of claim 1 wherein the concentration of said amine is about 1 to 100 millimolar.

5. The kit of claim 1 wherein the concentration of said thiazole is about 0.1 to 100 millimolar.

6. The kit of claim 1 wherein said buffer further contains about 0.1 to 2.0 millimolar magnesium chloride.

7. A method for detecting an analyte comprising:
   a) combining a liquid suspected of containing an analyte with a first antianalyte immobilized on a solid support;
   b) blocking any unoccupied binding sites on said support with an inert protein;
   c) contacting the support blocked with said inert protein with a second antianalyte conjugated to intestinal alkaline phosphatase whereby binding takes place between said first and second antianalytes and said analyte to give a bound fraction including said intestinal alkaline phosphatase on said support;
   d) separating said support with said intestinal alkaline phosphatase from said first liquid;
   e) contacting said support with a composition comprising levamisole, a substrate for said alkaline phosphatase and a buffer including 2-amino-2-methyl-1-propanol said substrate being converted by said alkaline phosphatase on said support to a colored product; and
   f) detecting said analyte by formation of said colored product.

* * * * *